US012233252B2

(12) United States Patent
Tsui et al.

(10) Patent No.: US 12,233,252 B2
(45) Date of Patent: Feb. 25, 2025

(54) SUTURELESS INFLOW CANNULA ASSEMBLY FOR CONNECTING VENTRICULAR ASSIST DEVICES TO HUMAN CIRCULATION

(71) Applicant: 3R Life Sciences Corporation, Campbell, CA (US)

(72) Inventors: Steven Shi Lap Tsui, Kaohsiung (TW); Pong-Jeu Lu, Kaohsiung (TW)

(73) Assignee: 3R LIFE SCIENCES CORPORATION, Campbell, CA (US)

( * ) Notice: Subject to any disclaimer, the term of this patent is extended or adjusted under 35 U.S.C. 154(b) by 451 days.

(21) Appl. No.: 17/695,390

(22) Filed: Mar. 15, 2022

(65) Prior Publication Data

US 2022/0296874 A1 Sep. 22, 2022

Related U.S. Application Data

(60) Provisional application No. 63/162,086, filed on Mar. 17, 2021, provisional application No. 63/162,098, filed on Mar. 17, 2021.

(51) Int. Cl.
*A61M 60/863* (2021.01)
*A61M 60/165* (2021.01)
(Continued)

(52) U.S. Cl.
CPC ........ *A61M 60/863* (2021.01); *A61M 60/165* (2021.01); *A61M 60/178* (2021.01); *A61M 60/268* (2021.01); *A61M 60/31* (2021.01); *A61M 60/32* (2021.01); *A61M 60/427* (2021.01); *A61M 60/515* (2021.01); *A61M 60/531* (2021.01); *A61M 60/546* (2021.01);
(Continued)

(58) Field of Classification Search
CPC .............. A61M 60/178; A61M 60/859; A61M 60/561; A61M 60/863
See application file for complete search history.

(56) References Cited

U.S. PATENT DOCUMENTS

| 7,258,679 B2 * | 8/2007 | Moore ................ A61M 60/268 604/164.11 |
| 7,846,123 B2 | 12/2010 | Vassiliades et al. |

(Continued)

FOREIGN PATENT DOCUMENTS

WO 2021137805 A2 7/2021

OTHER PUBLICATIONS

International Searching Report and Written Opinion issued Jun. 6, 2022 in PCT Application No. PCT/US 2022/020414.

*Primary Examiner* — George R Evanisko
(74) *Attorney, Agent, or Firm* — Muncy, Geissler, Olds & Lowe, P.C.

(57) ABSTRACT

An inflow cannula assembly intended for connecting a ventricular assist device (VAD) to a heart chamber without suturing anastomosis is provided. The inflow cannula assembly includes a deformable flow cannula with funnel-shaped bellmouth intake at a first end and a second end interfaced to the inlet of a VAD with minimal interface discontinuity; also includes is a pair of male and female fasteners that can be screw locked to fix and seal the cannula bellmouth against the endocardium for hemostasis purpose; as well as a VAD coupler and a VAD inlet adapter that enable a quick connection of the cannula with the VAD.

11 Claims, 24 Drawing Sheets

(51) Int. Cl.
*A61M 60/178* (2021.01)
*A61M 60/268* (2021.01)
*A61M 60/31* (2021.01)
*A61M 60/32* (2021.01)
*A61M 60/427* (2021.01)
*A61M 60/515* (2021.01)
*A61M 60/531* (2021.01)
*A61M 60/546* (2021.01)
*A61M 60/585* (2021.01)
*A61M 60/857* (2021.01)
*A61M 60/859* (2021.01)
*A61M 60/861* (2021.01)
*A61M 60/878* (2021.01)

(52) U.S. Cl.
CPC ........ *A61M 60/585* (2021.01); *A61M 60/857* (2021.01); *A61M 60/859* (2021.01); *A61M 60/861* (2021.01); *A61M 60/878* (2021.01); *A61M 2205/02* (2013.01)

(56) References Cited

U.S. PATENT DOCUMENTS

| | | |
|---|---|---|
| 9,138,228 B2 | 9/2015 | Vassiliades et al. |
| 2020/0023108 A1 | 1/2020 | Garrigue et al. |
| 2021/0339006 A1 | 11/2021 | Shambaugh, Jr. |

\* cited by examiner

SUTURELESS INFLOW CANNULA ASSEMBLY FOR CONNECTING VENTRICULAR ASSIST DEVICES TO HUMAN CIRCULATION

BACKGROUND OF THE INVENTION

Field of the Invention

The application relates in general to an inflow cannula assembly, and in particular to a cannula assembly that includes a deformable cannula.

Description of the Related Art

Mechanical circulatory support system such as ventricular assist device (VAD), in particular the left ventricular assist device (LVAD), has evolved into a standard care modality for treating advanced heart failure. Currently, the heart failure patients indicated for VAD application are those who are irresponsive to medical therapy, being classified as terminal stage with imminent death threat if without heart transplant or mechanical circulatory support. To date, the worldwide VAD registry has exceeded 25,000 implants since the approval of the continuous-flow durable LVADs (rotary pumps) including Heartmate 2, Heartmate 3 and HVAD. It is anticipated that the use of LVADs as advanced heart failure therapy will receive more acceptance along with further advancement of the VAD technologies.

Implantation of VAD generally requires an inflow and an outflow cannula be established for connecting VAD, in-series or in-parallel, to the device recipient's native circulation system. In-parallel connection has been widely accepted by VAD implantation because of its anatomic and hemodynamic advantages. For such prosthetic flow circuit establishment, inflow cannula is placed with its first end connected to the ventricle or atrium and the second end to the VAD inlet. Blood flow, hence, is withdrawn from the heart (ventricle or atrium), entering into and being energized by the pump actuator, and finally returns via the outflow cannula to the large artery of the assisted circulation. Surgically, the establishment of LVAD inflow cannula is most invasive and skill dependent, commonly requiring coring a large hole (20-30 mm in diameter) through the ventricular apical wall, followed by a carefully planned and time-consuming suturing process for fixation and seal of the inflow cannula around the cored myocardial wall. Intraoperative bleeding and air embolization at suturing site have been generally associated with the anastomotic skills and experiences of the surgeon. Pump malposition or migration, occurring peri- or post-operatively, have been related to the inflow cannula design and the insertion planning and execution as well. The cannula implantation related adverse events include, but are not limited to, perioperative surgical bleeding and the postoperative inflow obstruction and thrombotic complications. Often, such cannula-induced complications may result in devastating postoperative pump thrombosis, thromboembolism and infarction in organs, as well as serious stroke or neurological injury and cerebral dysfunctions.

A representative example showing a centrifugal rotary pump 10 implanted to a left ventricle (LV) is illustrated in FIGS. 1A to 1C. In general, the rotary pump 10 comprises an inflow cannula 11, an outflow cannula 15, a rotor or impeller 12 in which embedded with a permanent magnet, a stator 13 wound with electric coils, and a controller 14 that regulates the rotor speed for designated blood flow delivery. With the spinning of the rotor 12, hemodynamic suction is generated to drain the blood stored in the left ventricle (LV) chamber via the inflow cannula 11 into the rotary pump 10. This pump inflow will be energized by the impeller-actuated mechanical energy conversion process, flowing through the impellor and collected in the volute 16 and finally delivered from the outflow cannula 15 into the aorta Ao to assist circulation. Likewise, other types rotary pumps, adopting axial or diagonal flow design, will have similar inflow and outflow cannula design for bypassing the blood flow through the artificially established bypass flow route. For the LVAD implantation shown in FIGS. 1A to 1C, a coring of LV apex is first performed to create a through-hole 61 in the myocardial wall, then a sleeve anchor 111 is inserted and sutured around the through-hole 61, working as an adapter to receive the inflow cannula 11 of the LVAD. Such inflow cannula establishment involves with several intraoperative surgical risks and postoperative cannula-induced complications, as explained in the following.

Comparing to pump actuator design, inflow and outflow flow characteristics and cannula design have been less studied. As a rule of thumb, the guidelines for inflow cannula design suggest that, first, it ought to protrude above the endocardium of the ventricular wall and second, be oriented to point at the mitral valve and in parallel to the interventricular septum 62, as shown in FIG. 1A. The first guideline was suggested based on the past experiences that a short inflow cannula 11 with tip lower than the endocardium (see FIG. 1B) often caused myocardial tissue 63 in-grown into the cannula 11, resulting in a progressive pannus overgrowth and obstruction of the inflow tract. In addition, in-situ clot will be formed on top of these in-grown tissues 63 and dislodged into the pump-propelled blood stream, becoming the sources of thromboembolism related complications including cerebral dysfunction, stroke, and visceral organ infarction. The second guideline arose as to prevent inflow cannula from inclining toward the ventricular septum 62, which, if not properly implemented, would impede inflow entrainment, jeopardize support efficacy, and induce detrimental low-speed flow in the pump leading to pump thrombosis. As a matter of fact, these two cannula insertion guidelines are mutually exclusive. A longer inflow cannula 11 tends to satisfy the first protrusion requirement but may incur flow blockage penalty if the cannula is misaligned slightly by a few angular degrees.

Clinically, often a diseased heart is ill-shaped with irregular wall thickness distribution, or pathologically dilated and presented with fibrotic or weakened tissues. The inflow cannula 11 establishment, hence, often encountered practical difficulty in implantation. Frequently, the suggested location of insertion and the actual orientation of the pump implant may deviate from what is originally planned. Moreover, even if the inflow cannula 11 is positioned as planned, the altered intraventricular morphology (protruded cannula in the ventricular chamber) may dismantle the native vortex structure and hence hamper the washout effect inside the ventricular chamber, or generates low-speed or recirculated flow zones around the protruded cannular root (see FIG. 1C), predisposing the ventricular chamber to become a thrombogenic origin. In other words, the inflow cannula configuration and the corresponding surgical method or cannula-induced perturbed blood flows in the ventricle are the causal factors leading to pump thrombosis and the resultant thrombotic complications.

The present invention aims to design a novel inflow cannula that enables an easier and safer insertion procedure without reliance on skill-dependent suturing, and in the meantime, improves intraventricular hemodynamics to mitigate all the aforementioned device-induced thrombotic complications associated with the existing LVAD inflow cannula design.

BRIEF SUMMARY OF INVENTION

To address the deficiencies of conventional ventricular assist device (VAD) inflow hemodynamics, an embodiment of the present invention provides an inflow cannula assembly, for transporting blood between a heart chamber and a VAD, including a deformable polymeric cannula, a pair of male and female fasteners, a VAD coupler, and a VAD inlet adapter. The cannula includes: a first end, with a bellmouth intake to be inserted into heart chamber; a second end, with a flange ramp configured to interface with an inlet adapter of the VAD; and a flow conduit, wherein the first and second ends are interconnected by the conduit, and the entire inner surface of the cannula is smooth and seamless. The male and female fasteners are screw interconnected with the male fastener anchored on the cannula. The VAD coupler connects the second end with the VAD inlet adapter, and the VAD coupler includes a flange base and a pair of collars pinned on the flange base, wherein the collars have an internal grooved slot to receive and compress the sandwiched flange base, the flange ramp of the cannula, and a beak flange of the VAD inlet adapter; and the VAD inlet adapter includes a wedge-shaped beak to be interfaced with the second end, the beak flange to be accepted by the coupler, and a base integrated with the VAD.

In some embodiments, the bellmouth has a gradually thinning wall thickness toward its tip, and the tip is literally sharp-edged.

In some embodiments, an overlay portion of the conduit in contact with a cored myocardium is roughened so as to promote cell and tissue ingrowth for hemostasis and immobilization purposes.

In some embodiments, porous materials are attached to the female fastener cap in contact with an epicardium for promoting cell and tissue ingrowth for hemostasis and immobilization purposes.

In some embodiments, the beak of the VAD inlet adapter and the second end of the flow cannula are interfaced over the flange ramp, with the inner diameter of the beak slightly larger than the inner diameter of the flow conduit, wherein an interface surface of the flange ramp is inclined generally 30 to 60 degrees to a centerline of the cannula.

In some embodiments, the VAD coupler includes an anti-decoupling latch and a collar contour that catches simultaneously onto the entire peripheral rim of the flange base during the closing of the collars for locking purpose.

In some embodiments, the inflow cannula assembly further includes a stent embedment disposed in the cannula.

In some embodiments, the stent is made of Nitinol material.

In some embodiments, the stent has a zig-zag ring structure, and the stent is distributed over regions covering the bellmouth and the conduit.

In some embodiments, the stent includes a plurality of arrays of zig-zag rings, wherein the arrays of zig-zag rings having a tubular shape being disposed in the conduit and a cone-shaped array of zig-zag rings disposed in the bellmouth.

BRIEF DESCRIPTION OF DRAWINGS

The invention can be more fully understood by reading the subsequent detailed description and examples with references made to the accompanying drawings, wherein.

DETAILED DESCRIPTION OF INVENTION

The making and using of the inflow cannula embodiments of the assist devices are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Unless defined otherwise, all technical and scientific terms used herein have the same meaning as commonly understood to one of ordinary skill in the art to which this invention belongs. It should be appreciated that each term, which is defined in a commonly used dictionary, should be interpreted as having a meaning conforming to the relative skills and the background or the context of the present disclosure, and should not be interpreted in an idealized or overly formal manner unless defined otherwise.

Figure 2A:
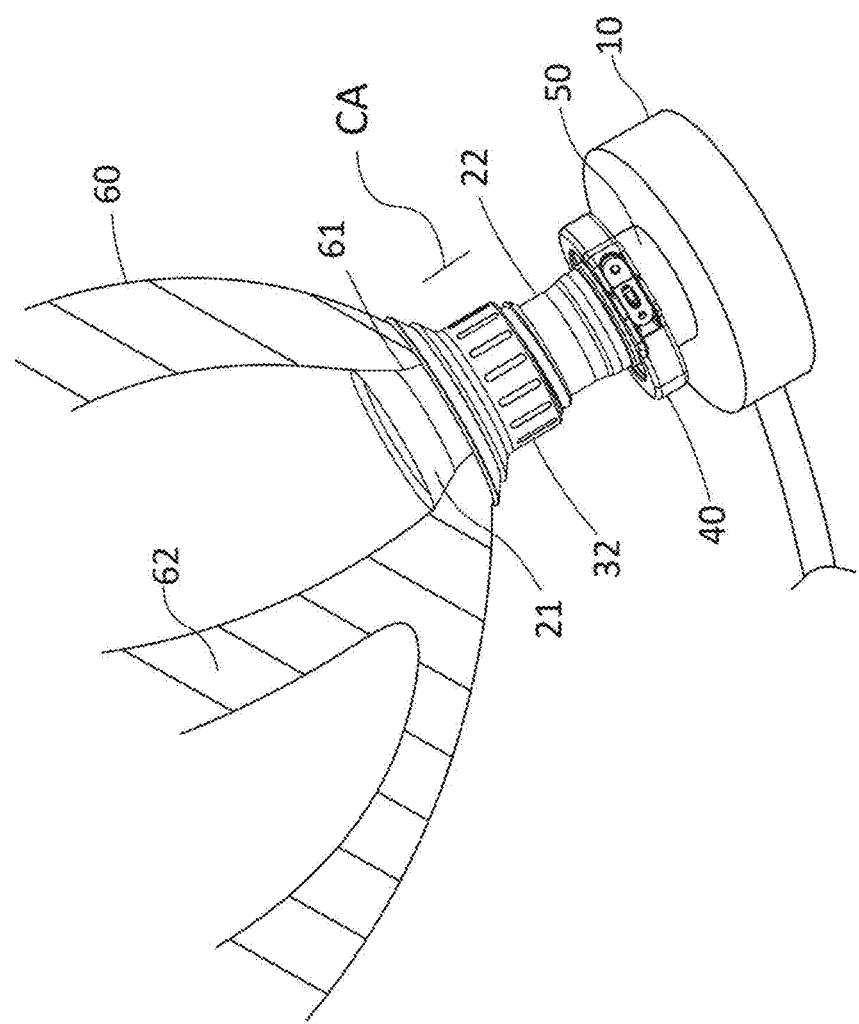
FIG. 2A is a perspective view of the present integrated inflow cannula assembly as mounted onto a rotary pump VAD.
Figure 2B:
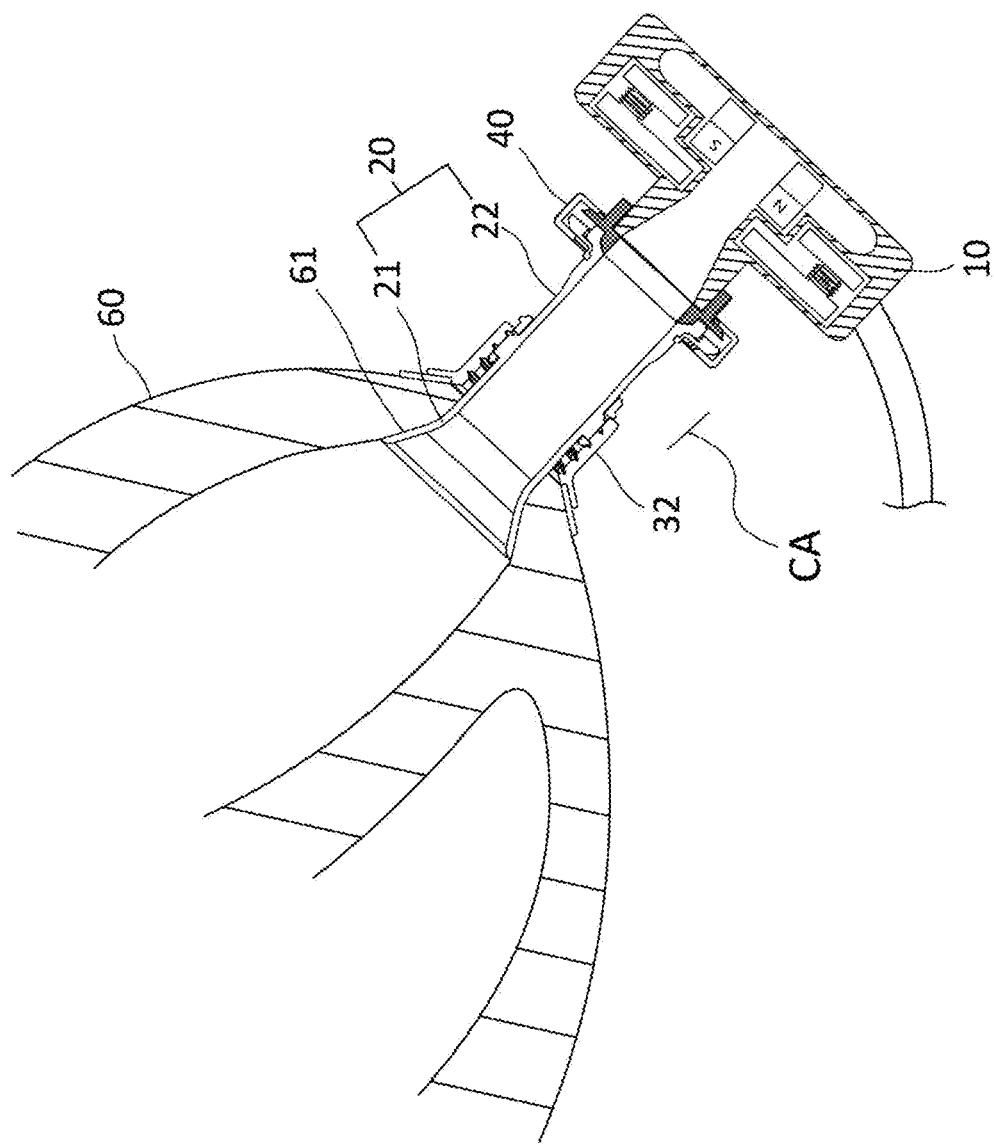
FIG. 2B is a sectional view of the integrated inflow cannula assembly as mounted onto a rotary pump VAD.

As shown in FIGS. 2A and 2B, an embodiment of the present inflow cannula assembly CA for connecting a ventricular assist device (VAD) 10 to a heart 60. This inflow cannula assembly includes a deformable polymeric cannula 20, a pair of male and female fasteners 31, 32, a VAD coupler 40, and a VAD inlet adapter 50. FIG. 2A schematically shows how an inflow cannula 20 of a rotary pump is connected to left ventricle, whereas a sectional view illustrating the flow passage and the interconnected cannula assembly components with respect to a centrifugal type VAD is provided in FIG. 2B.

The distal orifice, defined as the farther cannula end viewed from the connected VAD 10, is configured in a bellmouth 21 (the first end of the cannula 20) extension of the cannula 20 with gradually increasing cone diameter. The cone angle of this bellmouth 21 is typically 30-75 deg relative to the axis of revolution of the conduit 22. The central portion of the cannula 20 is the conduit 22 with an axi-symmetric cross sectional distribution. This said funnel-shaped cannula 20 constitutes a geometric locking mechanism when inserted across a cored through-hole 61 in the ventricular wall of the heart 60. Prior to the cannula 20 insertion, the original diameter of the through-hole 61 is generally in the range of 10-15 mm, which is substantially smaller than the outer diameter of the inserted conduit 22. Deformability of the present cannula invention, hence, is essential, which allows the cannula 20 be crimped into a smaller prepacked delivery form to facilitate insertion. Following bellmouth 21 insertion into the LV chamber and the release of the crimping constraints, the squeezed cannula 20 will restore to its original form having its conduit be snuggly embraced with oversize to the cored myocardial through-hole 61. Similarly, the bellmouth 21, as freed from crimping constraints, will self-expand and hence constitute an anti-dislodging anchorage against the contacted endocardium, as shown in FIG. 2B.

In some embodiments, the cored hole size (10-15 mm in diameter) required for the present cannula 20 implantation can be substantially smaller when compared to that of a rigid-walled inflow conduit (20-30 mm in diameter) pertaining to the contemporary rotary pumps. Excising lesser amount of tissue mass from the cardiac wall is surgically and anatomically advantageous. It not only reduces a permanent loss of contractile muscle, but also mitigates the risk of injury to papillary muscle and chordae tendineae that is responsible for atrioventricular valvular opening and closing as well as the associated valve flow regurgitation if the valve is not fully closed during systole.

There are two cardiac valves, namely aortic and mitral valves, situated in the left ventricle for regulating one-way flow into and out of the ventricular chamber. Notice that aortic valve regurgitation may impair VAD support efficacy and promote intraventricular thrombus formation. On the other hand, mitral valve regurgitation would lead to pulmonary congestion and hypertension, potentially causing pulmonary edema and death-threatening right heart failure. In recent years, rotary pump thrombosis complication was effectively annihilated using pump speed modulation strategy. As pump speed is lowered to allow intermittent valve opening and closing, a functional valve opening/closing is important. Coring-induced chordae tendineae and papillary muscle injury will adversely affect the valvular function, and the accompanying valve flow regurgitation may jeopardize the support efficacy as well as induce valve associated complications stated above. Hence, reducing the cored tissue volume around the LV apex, as the present invention does, may significantly improve the VAD implantation safety and efficacy and reduce the postoperative thrombotic event rate.

Figure 3A:
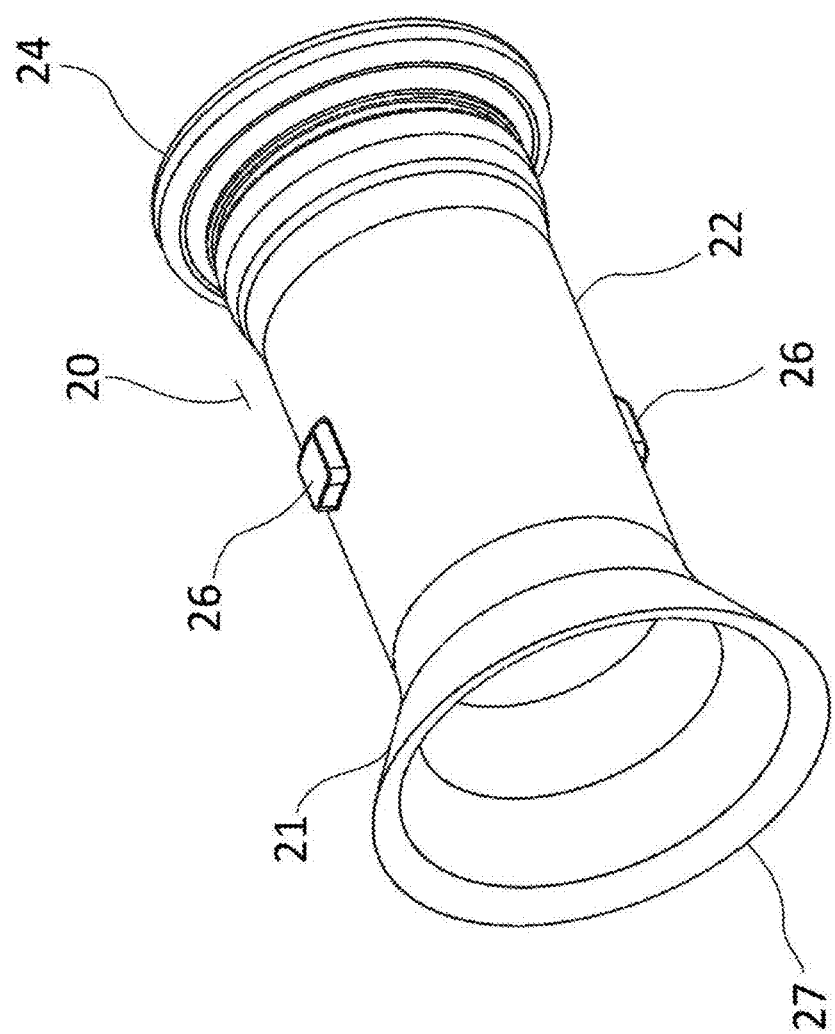
FIG. 3A is a perspective view of a polymeric inflow cannula conduit as an embodiment of the present invention. For clarity, velour on cannula conduit is not shown.
Figure 3B:
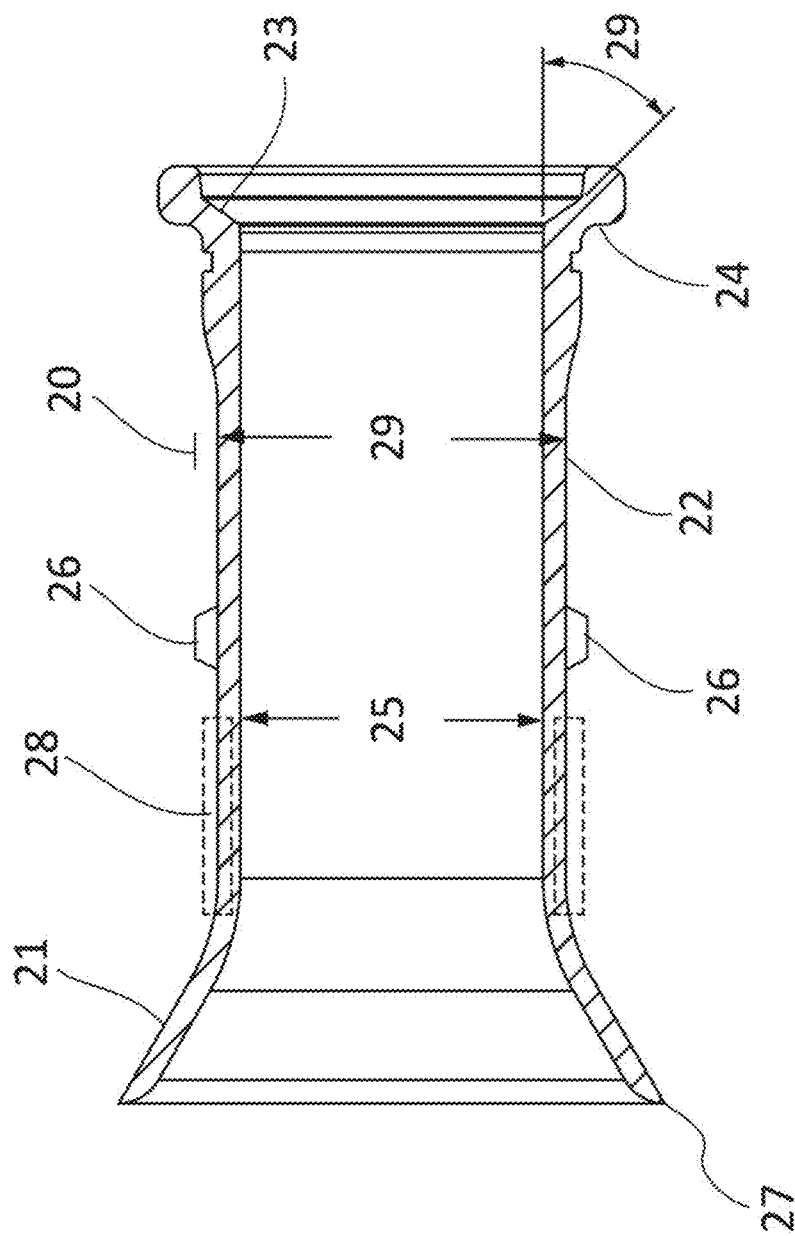
FIG. 3B is a sectional view of a polymeric inflow cannula conduit as an embodiment of the present invention.
Figure 4A:
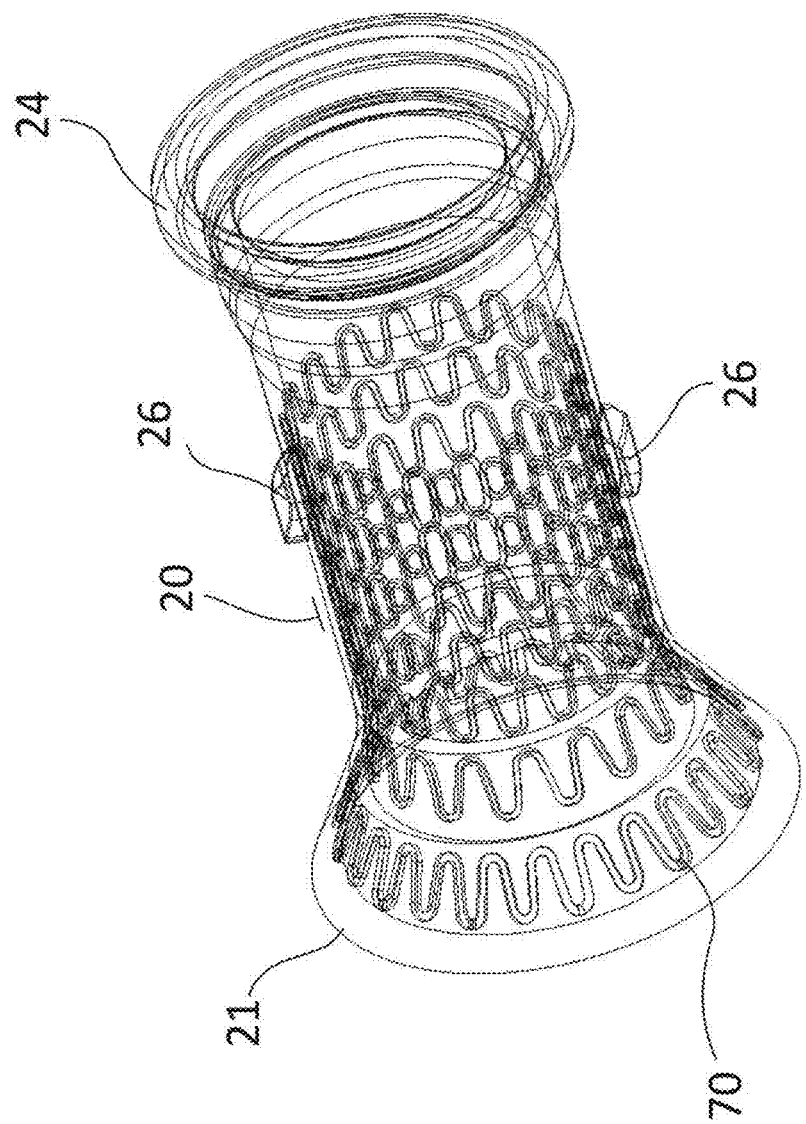
FIG. 4A is a perspective transparent view of a Nitinol stent-reinforced inflow cannula conduit as a preferred embodiment of the present invention.

Two embodiments of such funnel-shaped cannula 20 are shown in FIGS. 3A, 3B, and FIG. 4A, respectively. For these embodiments, polymeric elastomer such as silicone or polyurethane can be adopted as the material, which can be mold casted or injected into a seamless cannula with smooth blood-contacting surface. At the distal end of the bellmouth 21 is a sharp-edged tip 27 that can be attached to the endocardium with minimal geometric discontinuity. In addition, because the wall of the bellmouth 21 around its tip 27 end is gradually thinned, the rigidity of the bellmouth 21 reduces in proportion to the wall thickness toward the tip 27, rendering the bellmouth 21 flexible and shape-conformal when compressed against the endocardium. There are multiple protruded stubs 26 disposed in the middle region of the conduit 22 to allow locking engagement to the male fastener 31.

As shown in FIG. 3B, an overlay portion 28 of the conduit 22 in contact with the cored myocardium can be roughened to promote tissue ingrowth during the wound healing period. The surface of the overlay portion 28 can be made by attaching a felt with appropriate porosity or by depositing a thin layer of polymeric filaments generated, for example, by electrospinning. This rough overlay portion 28 can help immobilize or seal the implanted cannula 20 via tissue ingrowth and hence maintain a long-term hemostasis effectiveness postoperatively.

Another embodiment is to have the previous embodiment (FIGS. 3A and 3B) embedded with a stent 70 or a stent reinforcement, as shown in FIG. 4A. In some embodiments, the stent 70 is flexible, and has a metallic material, such as super-elastic Nitinol material. By embedding the stent 70 inside the cannula 20 wall, the wall thickness can be further thinned to decrease the outer diameters of the cannula 20 (including the bellmouth 21 and the conduit 22). Hence, the implantability of the stent-embedded cannula would be upgraded without compromising the hemodynamic performance which is dominated by the inner diameter 25 of the conduit 22. Moreover, the stent 70 may share a substantial amount of the pulsatile pressure loading exerted on the conduit 22, hence enhancing the conduit durability and safety. Mechanically, the stent 70 is able to endure large deformation without structural yielding that meets the foldability requirement of the present cannula 20.

Figure 4B:
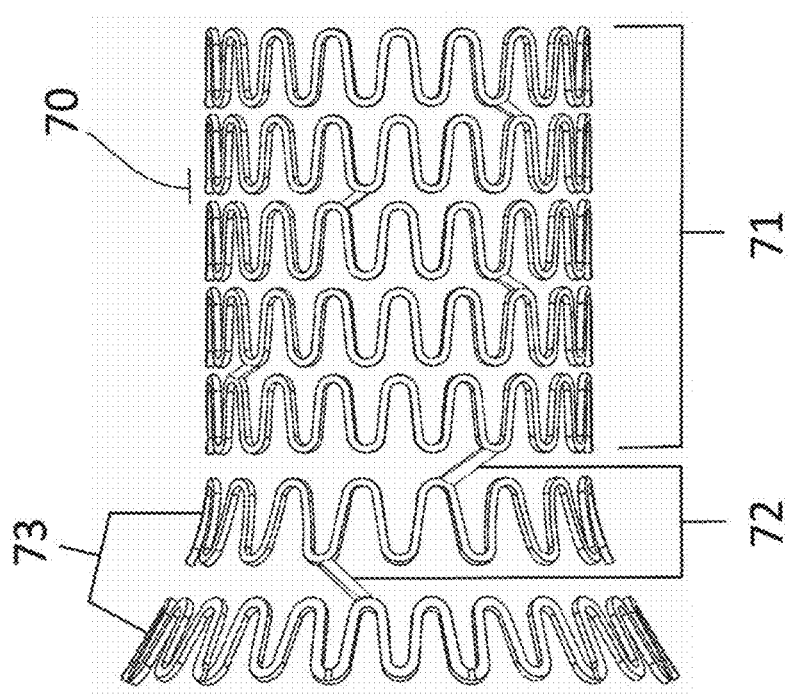
FIG. 4B shows a lateral view of the Nitinol stent embedment used in the cannula shown in FIG. 4A.
Figure 4C:
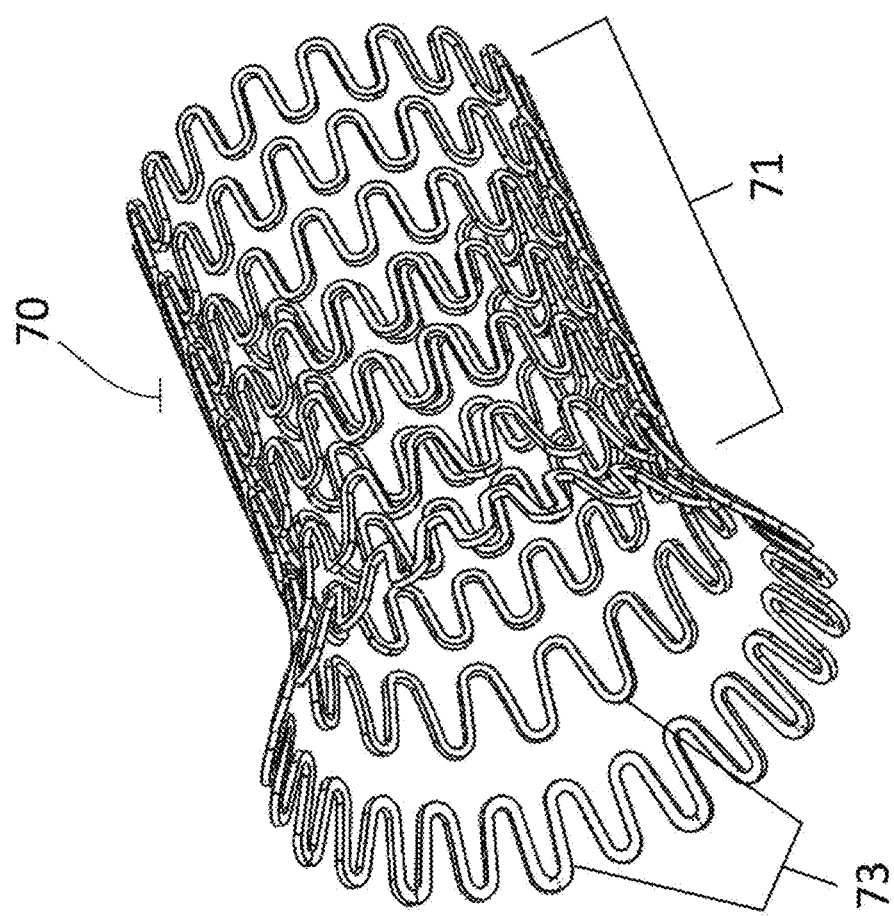
FIG. 4C shows a perspective view of the Nitinol stent embedment used in the cannula shown in FIG. 4A.

A lateral and perspective view of a representative Nitinol stent insert is illustrated in FIG. 4B and FIG. 4C, respectively. The stent 70 has a zig-zag ring structure, and includes a plurality of arrays of zig-zag rings 71, 73 and connection members 72.

The arrays of zig-zag rings 71, 73 are responsible for resisting the radial load, whereas the connection member 72 clusters the arrays of rings 71, 73 to resist the axial stretching force. In particular, the arrays of zig-zag rings 71 have tubular shape and are embedded in the wall of the conduit 22, whereas the arrays of rings 73 having cone-shaped structure are embedded in the wall of the bellmouth 21. For a thin-walled bellmouth 21 the radial strength is gradually weakened along with the increase of the cone diameter toward the distal tip 27. Notice that when bellmouth 21 is locked with female fastener 32, insufficient radial strength in bellmouth 21 may lead to structural buckling and loss of shape-conformality, resulting in massive bleeding in use. The stent 70 can improve this polymeric material strength by providing sufficient anti-buckling capability without a need to increase the wall thickness of the bellmouth 21.

Figure 4D:
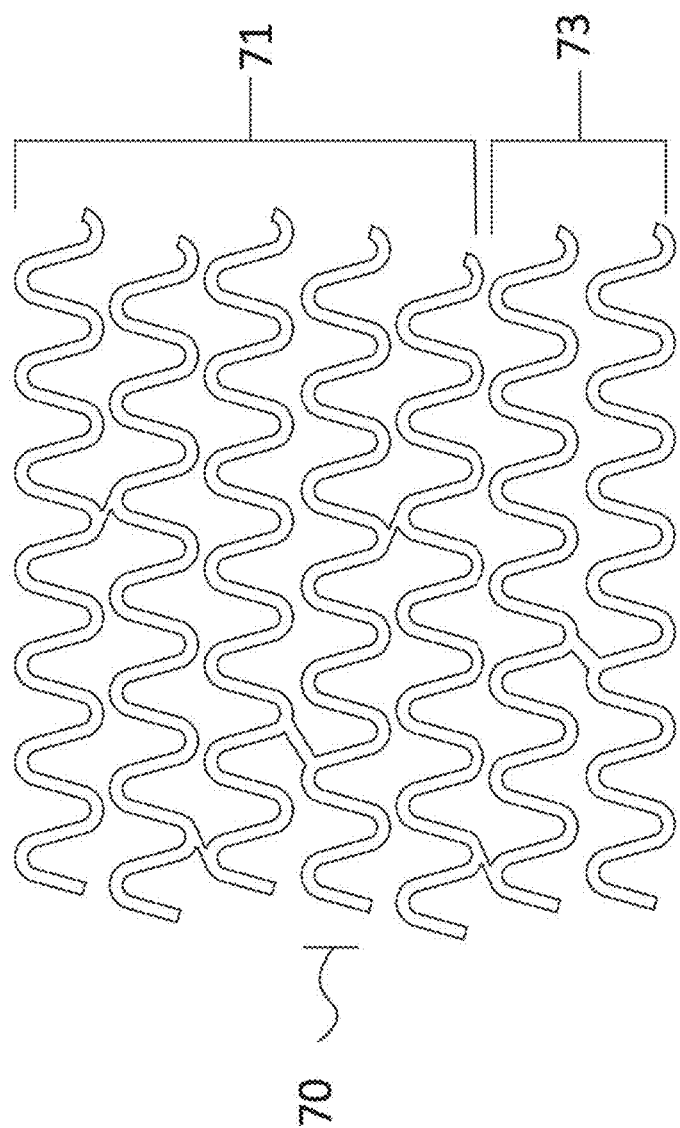
FIG. 4D shows a Nitinol stent embedment of FIG. 4C before expansion as depicted in a planar expanded view.

In the manufacturing of the stent 70, an array of interconnected zig-zag ring structure 71, 73 is first cut out from a thin-walled, straight Nitinol tube using a laser cutter. This tubular zig-zag array structure is shown in FIG. 4D in an expanded planar view. Following the standard expansion and heat treatment process the tubular array assembly 71, 73 can be step-by-step shaped into the stent 70 having a bellmouth intake. Surface grinding and electronic polishing are subsequently applied to remove the oxidized outer layer formed on the heat-treated surface of the stent 70. The final product is accomplished by mold co-injection of stent 70 with silicone or polyurethane elastomers, as illustrated in FIG. 4A.

Unlike the existing inflow cannula attachment designs that commonly require 10-12 suture stitch pairs, circumferentially placed around the cored myocardial hole 61, to attach a VAD 10 onto a heart 60, the present invention innovates a sutureless fixation approach. Conventional suture fixation relies on the tension force generated in the string by pulling tight the anchored suture pair. In a sharp contrast, the present sutureless pump attachment adopts a completely different fixation and force generation mechanism provided by a fastener pair 31, 32. This new attachment design simultaneously locks and seals the inflow cannula 20 with respect to the connection site myocardium. Sutureless fixation of cannula 20 to the contacted myocardium is accomplished by a pair of male and female fasteners 31, 32, which are shown in FIGS. 5A, 5B and FIGS. 6A to 6D, respectively.

Figure 5A:
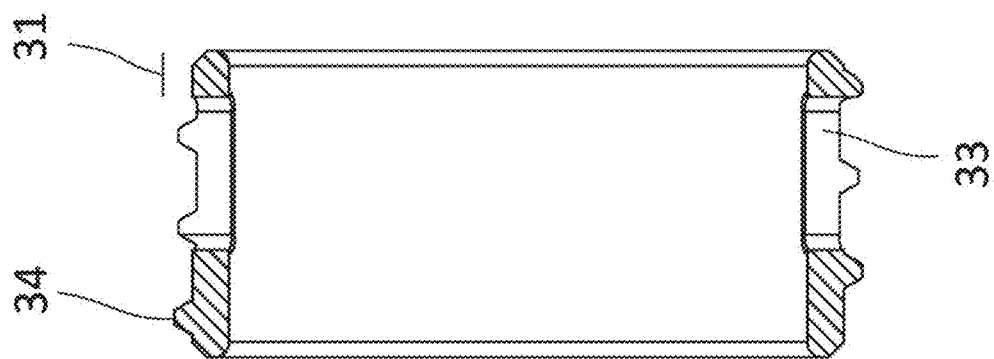
FIG. 5A is a lateral view of the male fastener component.
Figure 5B:
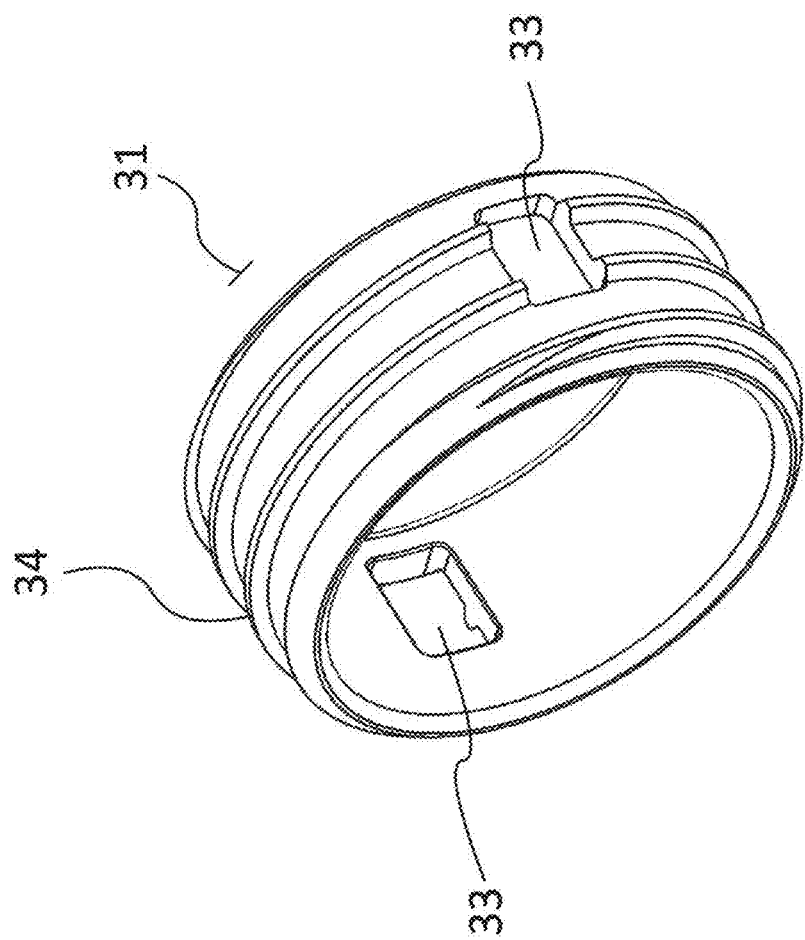
FIG. 5B is a perspective view of the male fastener component.

Depicted in FIGS. 5A and 5B are the sectional and perspective views of the male fastener 31. A screw thread 34 is carved on the external surface of the male fastener 31, from end to end, with multiple slots 33 made approximately in the middle region of the male fastener 31. The inner diameter of the male fastener 31 is substantially equal, with a small clearance, to the outer diameter 29 of the cannula conduit 22. When mounted onto cannula 20, the protruded seats 26 on the conduit 22 will interlock with the slots 33 (FIG. 7) and thereby work as a support base to provide counteracting axial and lateral forces required for screw locking with the female fastener 32.

Figure 6A:
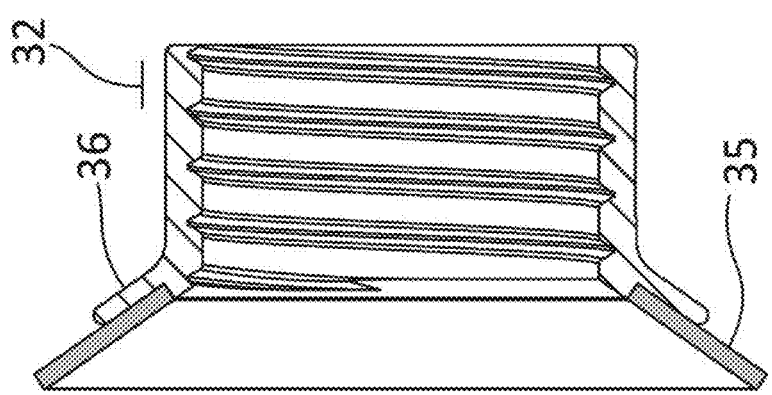
FIG. 6A is a sectional view of the female fastener component.
Figure 6B:
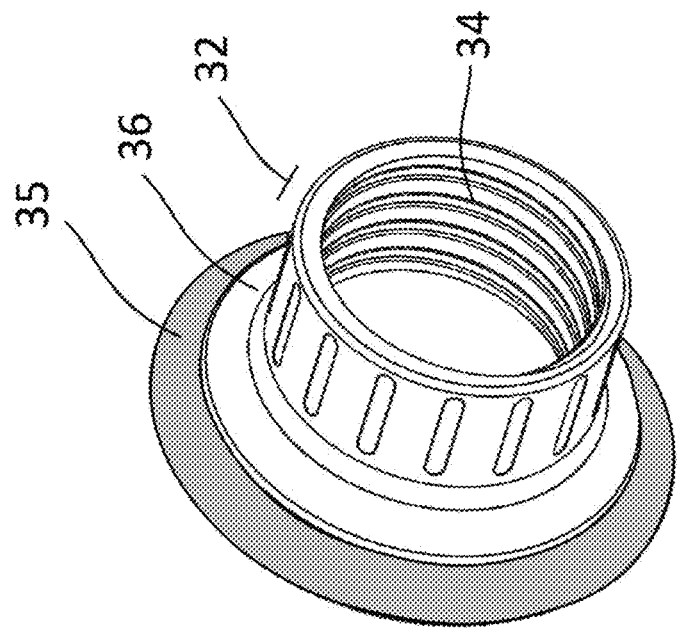
FIG. 6B is a frontal and rear perspective view of the female fastener component.
Figure 6B:
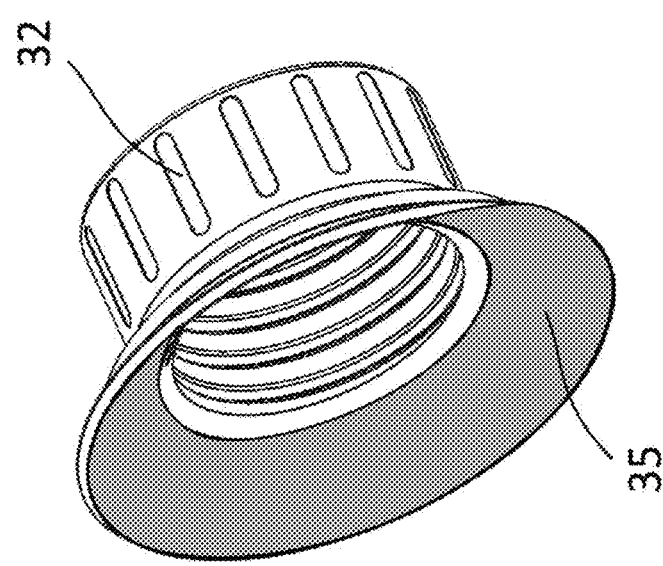

Referring to FIGS. 6A and 6B, the female fastener 32 is a lock nut having a funnel-shaped distal cap 36 to be compressed against epicardium for locking and seal purposes. The angle of the cap 36 is approximately equal to the angle of the bellmouth 21. As the screws of male and female fasteners 31, 32 are tightened together, compression force will be generated and evenly distributed in the sandwiched myocardium between the cap 36 and the bellmouth 21. Moreover, the cone of bellmouth 21 will deform slightly, in compliance with the fitted endocardium terrain, to simultaneously achieve the functions of seal (bleeding prevention) and cannula fixation. Around the outer rim of the cap 36, a cone cuff 35, made of surgical felt, is attached. The soft-contact porous feature provided by the felt is another guarantee of hemostasis. Tissues or cells may be ingrown into the void space in the cone cuff 35 along with the postoperative wound healing process. A few stay sutures can be placed around the cuff rim to further help fix the screwed female fastener 32 with the epicardium during the acute healing period.

Figure 6C:
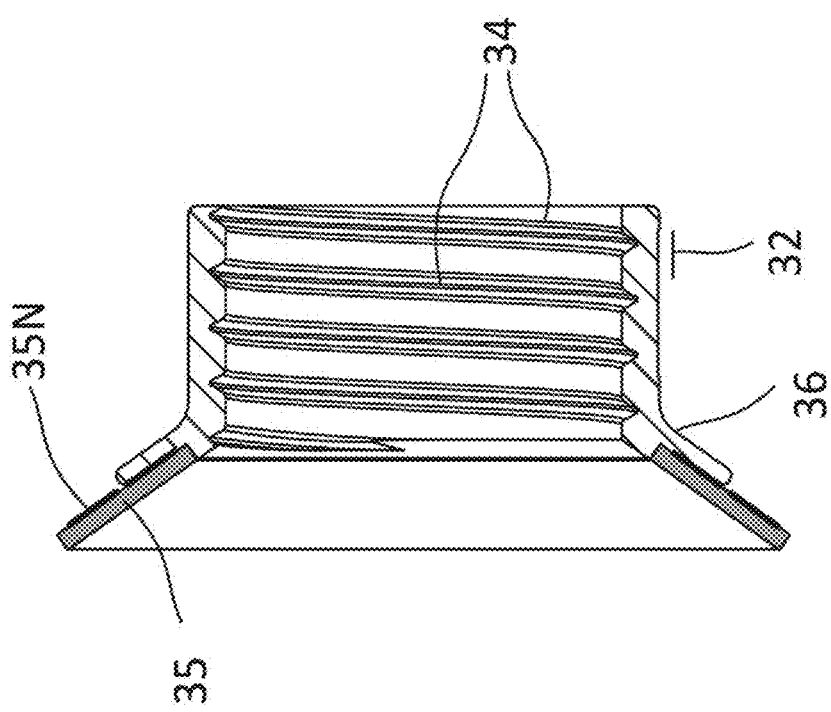
FIG. 6C shows a variant of the female fastener design depicted in FIG. 6A, of which the cuff is additionally supported by a Nitinol stent.
Figure 6D:
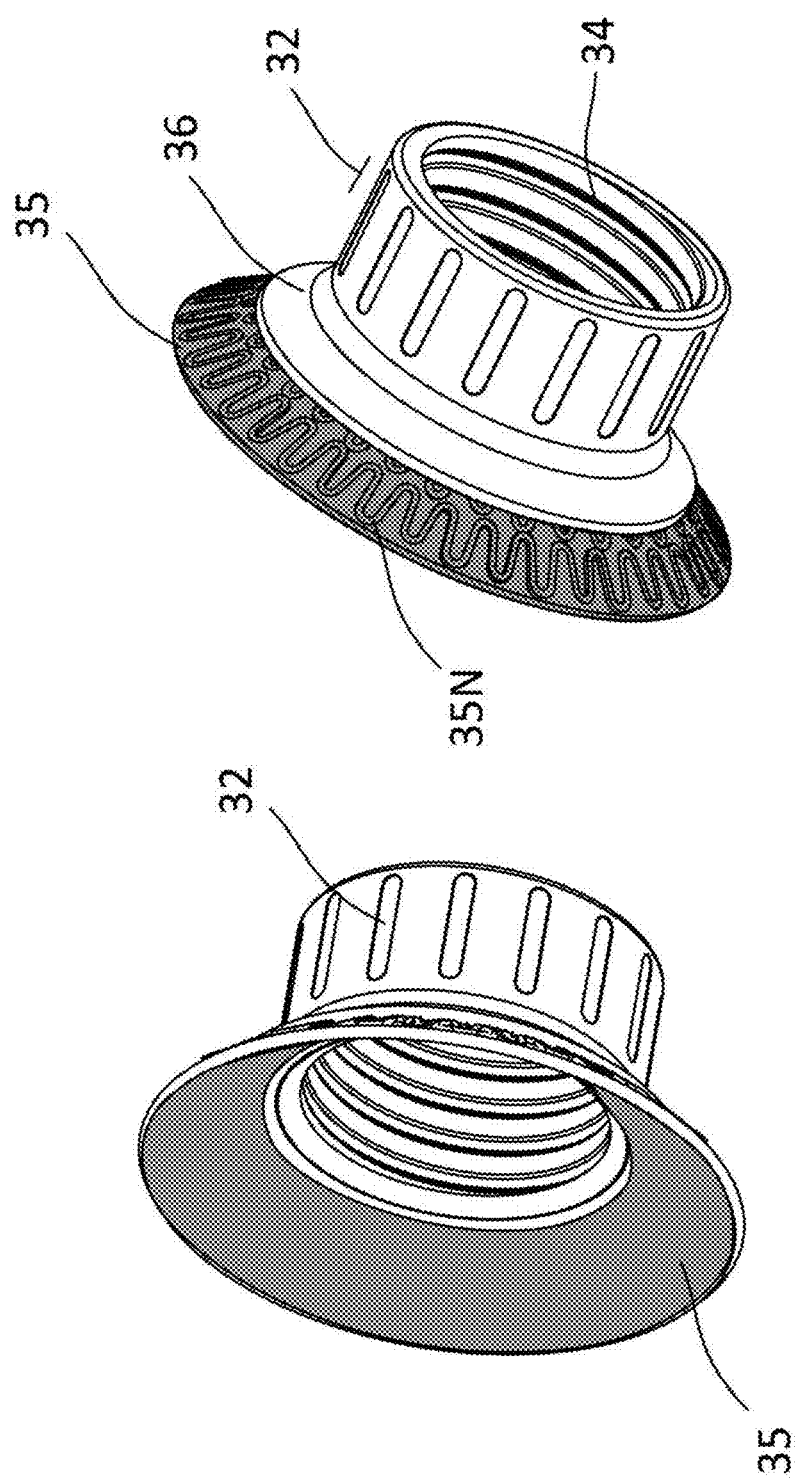
FIG. 6D shows a variant of the female fastener design depicted in FIG. 6B, of which the cuff is additionally supported by a Nitinol stent.

The present sutureless flow cannula implantation may encounter postoperative tissue atrophy at the clamped connection site. Such tissue atrophy will jeopardize the seal effectiveness and potentially causes bleeding at the connection site. In FIGS. 6C and 6D are shown another embodiment of the female fastener 32 intended to mitigate this atrophy-induced postoperative bleeding. The cuff 35 is additionally supported by a cone-shaped Nitinol stent 35N similar to that of the bellmouth stent 73 illustrated in FIGS. 4B and 4C. As the female fastener 32 is compressed onto the epicardium, the deformed super-elastic Nitinol stent 35N will provide a contact spring load to assure that the cuff 35 always adheres to the epicardium during the wound healing process, hence obviating the risk of postoperative atrophy-induced blood leak.

Figure 7:
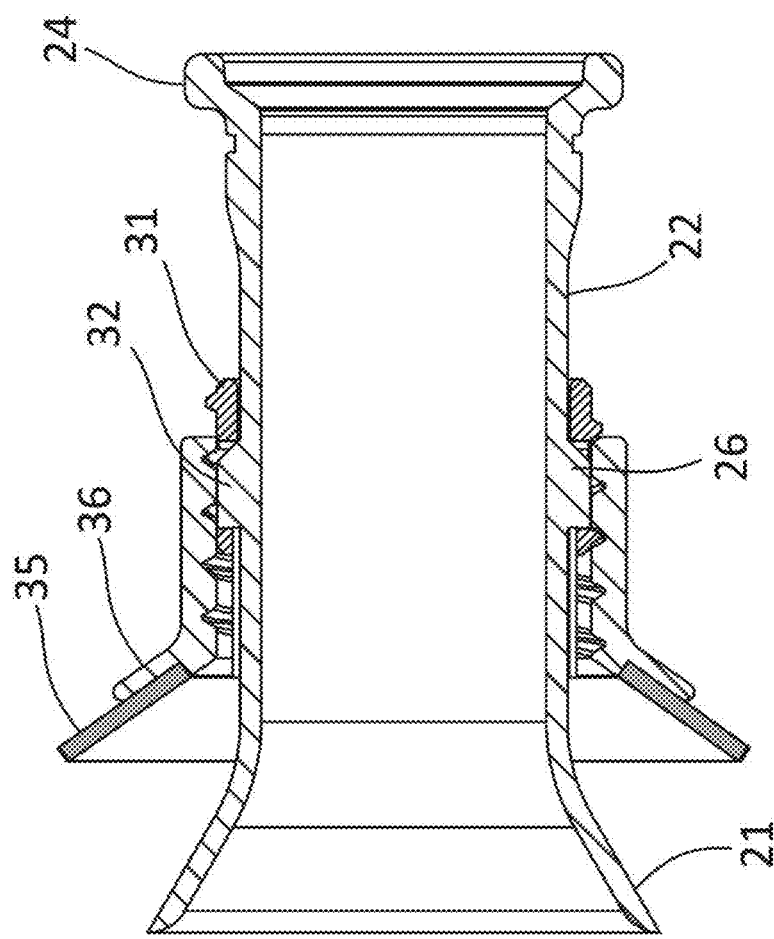
FIG. 7 is a sectional view of an integrated fastener in locking position with respect to the bellmouth and conduit body of an embodiment of the present cannula invention. For clarity, velour on the cannula conduit is not shown.

FIG. 7 shows the integrated fasteners 31, 32 as mounted on the cannula 20. Forces and strain involved in cannula deformation confers a special design feature of the present invention. Material elasticity consideration, in fact, need to be carefully incorporated in the present design. In mounting these fasteners onto the cannula body, the deformability ability of the cannula 20 is required as a prerequisite. The proximal or second end 24 (the flange ramp) of the cannula 20 ought to be crimped into a smaller profile so as to pass the end 24 through the ring-shaped fasteners 31, 32 sequentially. The male fastener 31 is first mounted and, along with the release of the crimped profile, locked onto the cannula conduit 22 via an engagement of those slots 33 in the fastener wall with the multiple protruded seats 26 on the conduit 22. The female fastener 32 is inserted following the same crimping and release of the cannula proximal end 24 and then screwed onto the male fastener 31.

Fixation of cannula 20 with heart 60 is accomplished by advancing the female fastener 32 forward until in contact with the epicardium with predetermined compression force. Suitable compression force required for a successful locking fixation and leakage seal can be determined by the surgeon or controlled using a torque wrench.

Mechanically, by screw tightening the male and female fasteners 31, 32, the bellmouth 21 and the cap 36 of the female fastener 32 will clamp the sandwiched myocardium from both sides across the insertion hole 61 to satisfy the fixation and leak-free requirements. It is worth noticing that the bellmouth 21 is shape-conformal to endocardium when compressed. The semi-rigid bellmouth 21 can be adaptively fit with the endocardial terrain, forming a seal barrier to obviate blood leakage concern. The male fastener 31 of the fastener pair, which is anchored on the protruded seats 26 of the conduit 22, however, works as a support base to counteract the locking force generated.

Figure 1A:
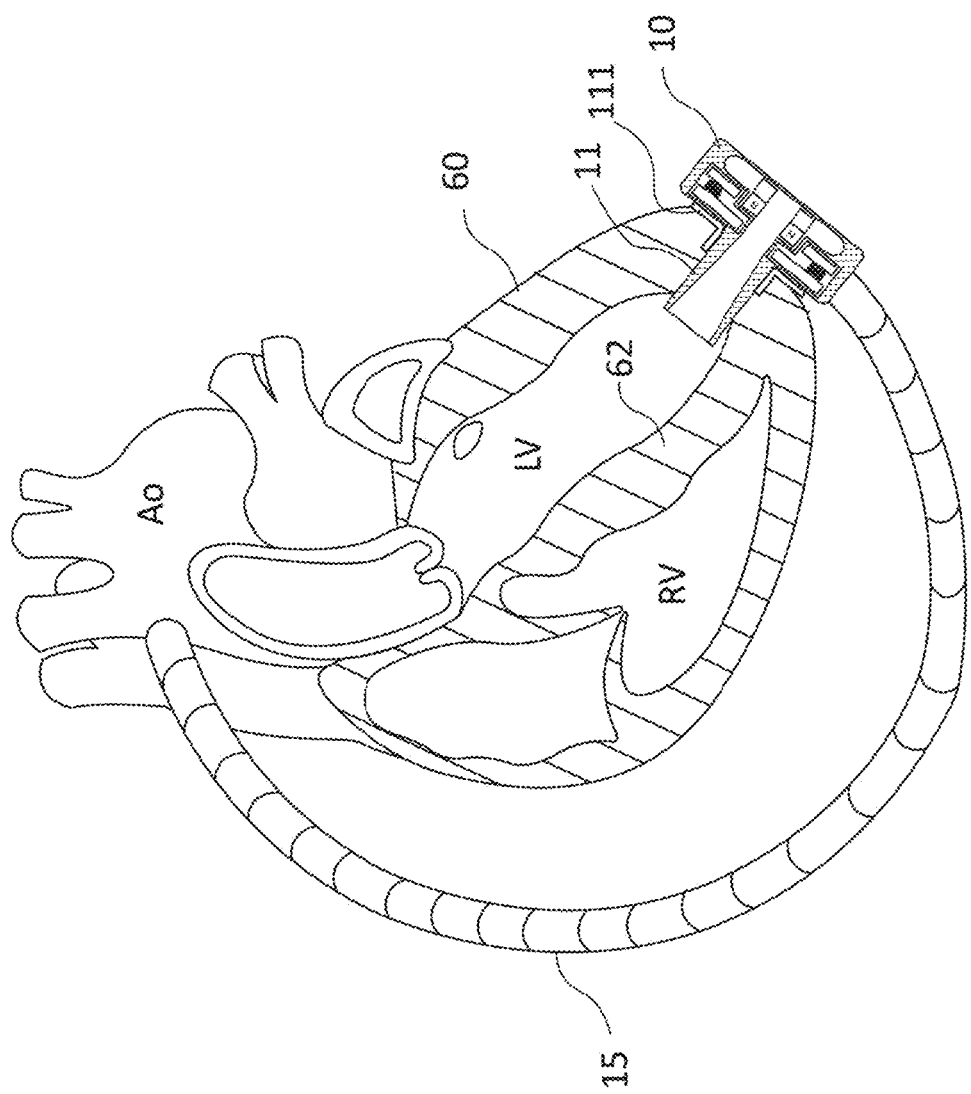
FIG. 1A is a schematic view of a rotary pump VAD implanted via a bypass route from left ventricular apex to ascending aorta.
Figure 1B:
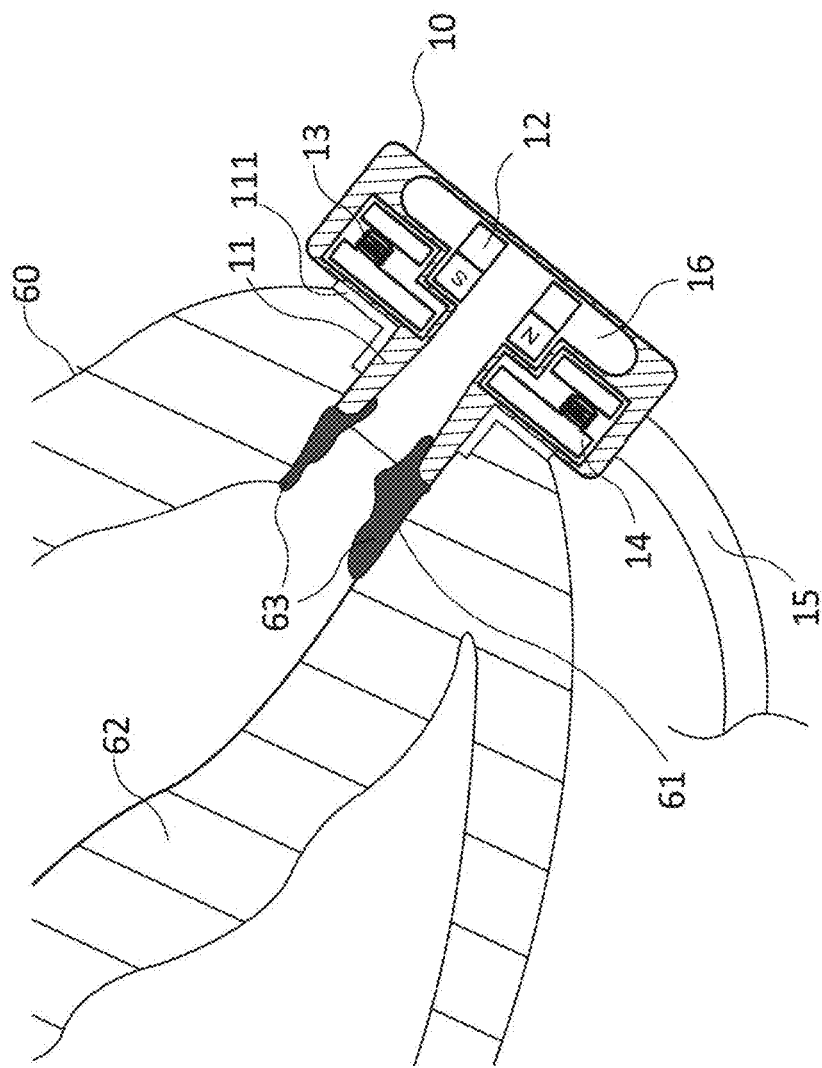
FIG. 1B illustrates an inflow cannula of a rotary pump connected to myocardium with a lower-than-endocardium insertion. In-grown tissue and in-situ clot formation is depicted, indicating the root cause of postoperative complications of inflow blockage and systemic thromboembolism.
Figure 1C:
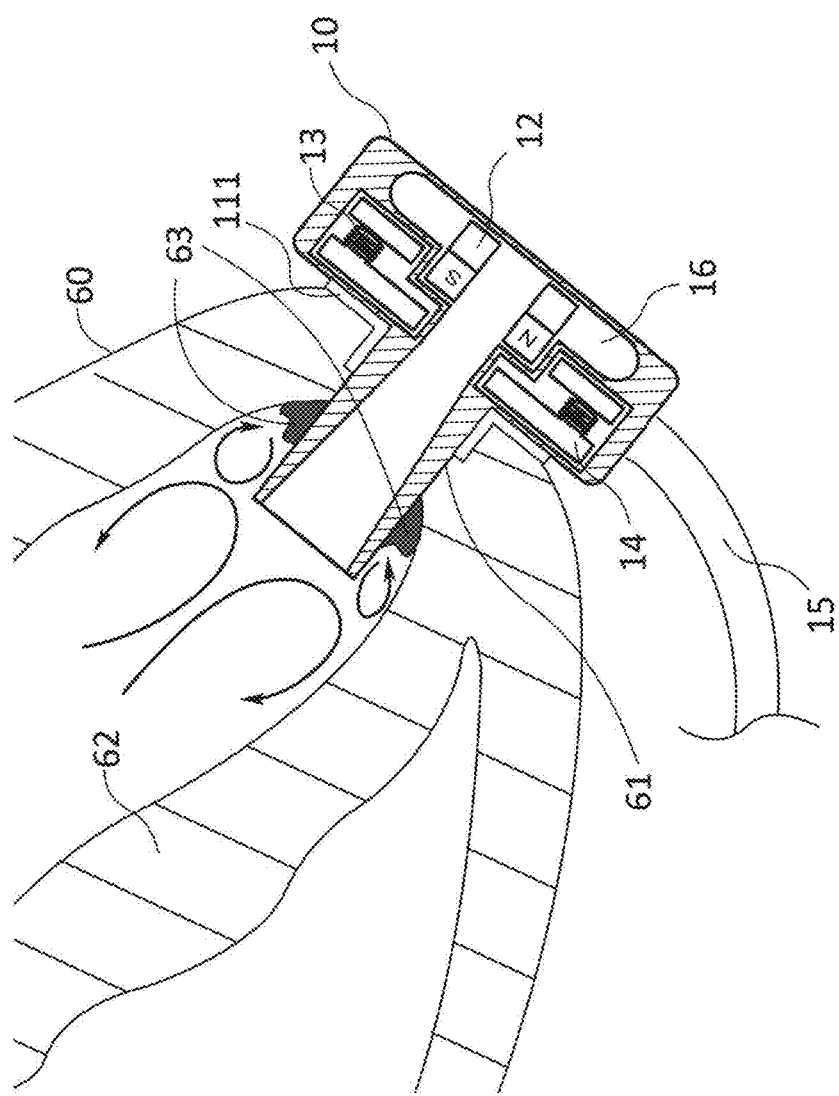
FIG. 1C illustrates a normal protrusion type inflow cannula connection to myocardium. Thrombotic neointima and clot may form around the root of the protruded cannula tip.

It is worth mentioning that the present sutureless attachment possesses an intrinsic positive feedback mechanism built for bleeding control. As ventricle contracts and ventricular pressure increases, the compression force acting on the bellmouth 21 will increase accordingly and better seal off the attached flow cannula 20. The concern of bleeding at hypertension is hence literally ruled out. This positive feedback effect is lacking in the conventional fixation by means of suturing as illustrated in FIGS. 1A to 1C. For conventional suture fixation, often, surgeon must check bleeding, based on a drug-induced temporary hypertension, after the completion of anastomotic suture attachment of the flow cannula 20. In FIG. 2B is illustrated a sectional view of how the present invention is in lock position with a connected ventricular wall. Compression type locking mechanism enables a distributed force be exerted around the clamped myocardial area in contact. The soft contact nature over bellmouth 21 and female fastener cap 36 avoids the traditional problem of suture string cutting generated within the stitched myocardium, which, often leads to bleeding through enlarged suture fissure at hypertension. Cardiac muscle is particularly vulnerable to string cutting associated with conventional suturing anastomosis, a problem that is much dependent on the mastery of suturing skills possessed by the surgeon.

Figure 8A:
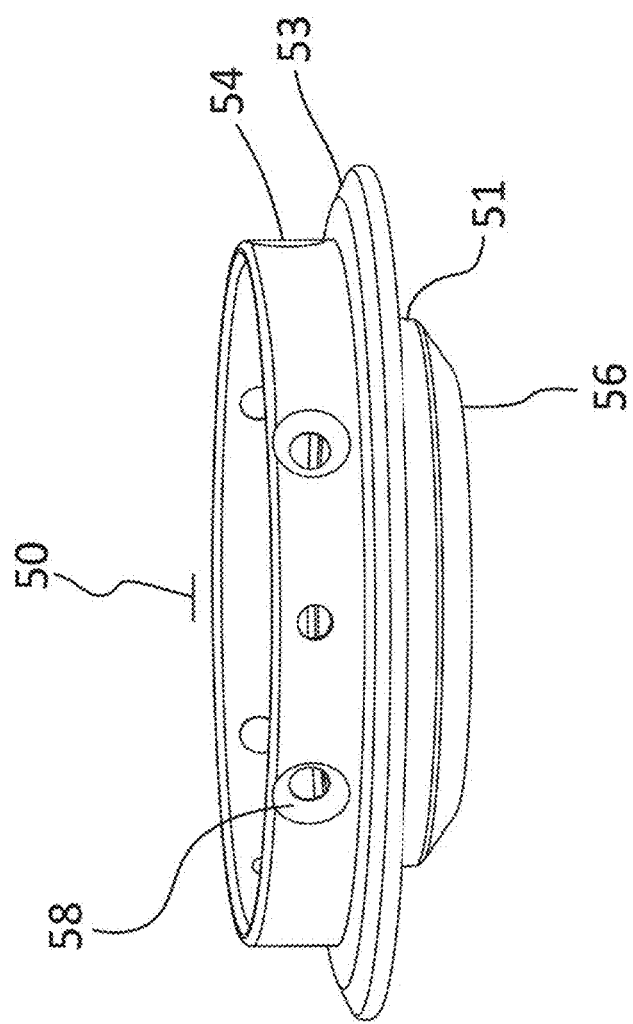
FIG. 8A is a perspective view of the VAD inlet adapter.
Figure 8B:
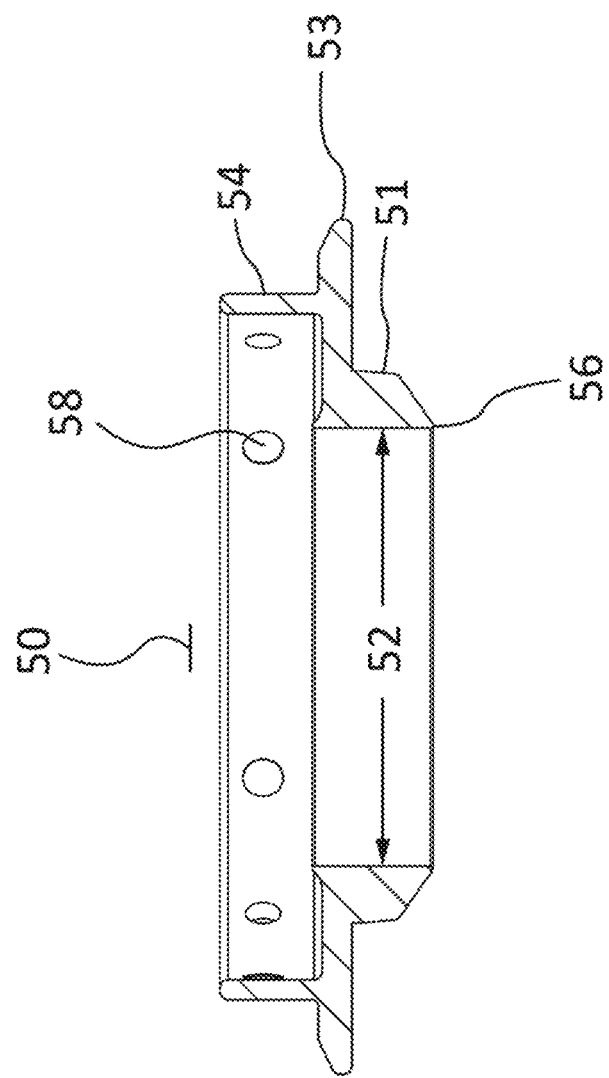
FIG. 8B is a sectional view of the VAD inlet adapter.

Around the proximal end 24 of the cannula conduit 20, the blood-contacting inner surface is configured to have a smooth geometric transition to the inlet of the connected VAD 10. As shown in FIGS. 8A and 8B, the VAD inlet adapter 50 is a body of revolution comprising a wedge-shaped beak 51, a beak flange 53 and a base 54, forming an extension of a VAD inlet housing. There are multiple eyelets 58 drilled on the base 54, which are used to integrate the inlet adapter 50 with the VAD 10. The beak 51, or the foremost part of the inlet adapter 50 of a connected blood pump or VAD, has an inner diameter 52 slightly larger than the inner diameter 25 of the flow cannula 20. Referring to FIG. 3B, in order to enhance the fault tolerance associated with step discontinuity generated at interface, the interface surface of the flange ramp 23 is sloped with an inclination angle 29 to the stream direction. Such ramp interface design keeps step or gap from being generated at interface surface of the flange ramp 23 due to limited manufacturing precision or matching concentricity associated with conventional butt connection. Nevertheless, this cone-shaped flange ramp 23 has an intrinsic shortcoming in fulfilling a concentric centerline alignment of the joined counterparts. This problem is solved by a special coupler design, as described below.

Figure 9A:
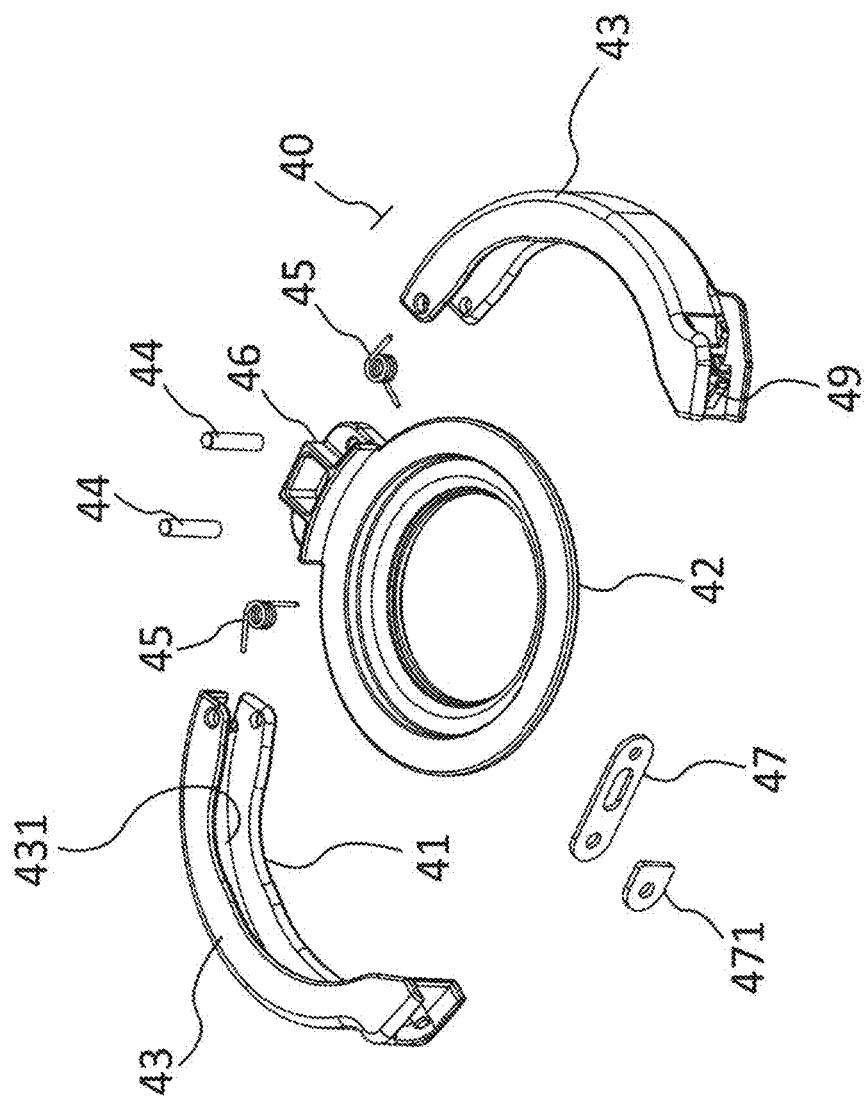
FIG. 9A is an exploded view showing the components of the coupler.
Figure 9B:
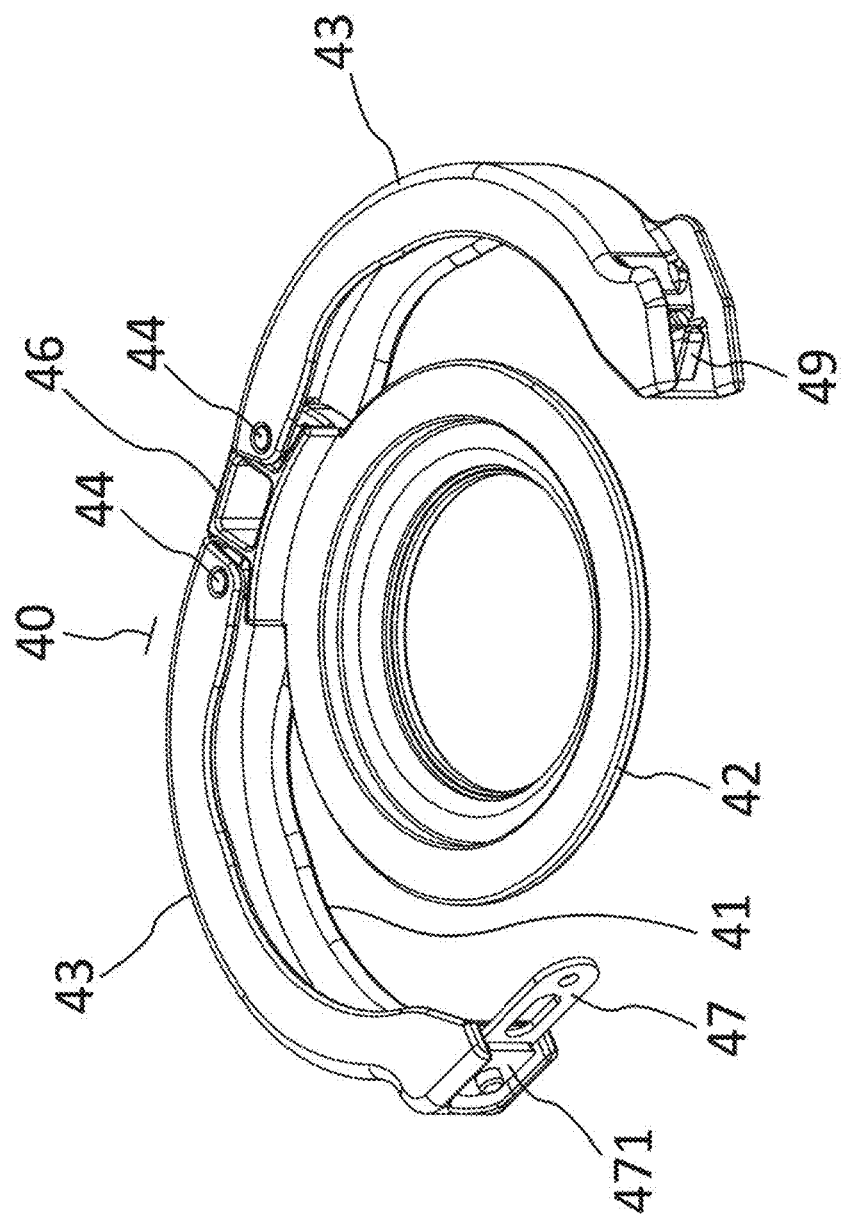
FIG. 9B is a perspective view of the coupler in an unlatched open form.
Figure 9C:
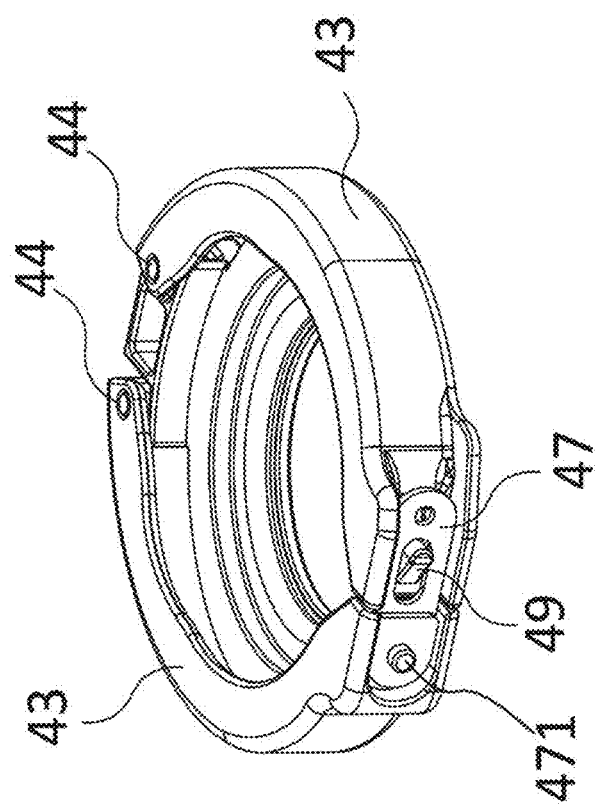
FIG. 9C is a perspective view of the coupler in a latched locked form.

The coupler 40, shown in FIGS. 9A to 9C, is specially designed in attempt to satisfy the hemodynamic and thromboresistance requirements when connecting the proximal cannula end 24 to the VAD inlet adapter 50. Illustrated in FIG. 9A are the components of the coupler 40 that constitutes the integration function. The coupler 40 includes a flange base 42, a pair of collars 43, and hinges 44 that join together the collars 43 with the flange base 42. Spring coils 45 are loaded in the hinge joint 46, maintaining the collars 43 in an opening position when unlocked (FIG. 9B). The collars 43 are grooved internally as shown in FIGS. 9A, 9B. The collars 43 have an internal grooved slot 431 to receive and compress sandwiched the flange base 42, the flange ramp 23 of the cannula 20, and the beak flange of the inlet adapter Quick-connection type locking can easily be carried out by closing the collars 43 that will be latched without a concern of unintentional unlocking, as depicted in FIG. 9C. A leaf spring type latch 47 is installed at the tip of one collar 43 by welding a slab 471 on top of the latch 47 to attain the required spring force. The latch 47 will be bent as it slides on a ramp 49 on the opposing collar in the course of locking. As latch 47 clears the top of the ramp 49, it will drop down to the base of said ramp 49 by an elastic restoring force, thereby working as a safe for preventing incidental latch unlock or collar opening ascribed to pump vibration or rocking in long-term use. For pump explant or exchange that requires component decoupling, the latch 47 can be bent and lifted upward by a tool, permitting an unlocking force to be exerted to rotationally open the collars 43 and hence disengage the VAD 10 from the cannula 20.

For the design of coupler 40 that is able to connect a rigid beak 51 with the semi-rigid cannula flange ramp 23 concentrically, a simultaneous catching around the entire peripheral rim of flange base 42 is critical. Whenever simultaneous catching/locking engagement fails to be accomplished, the initially caught cannula flange ramp 23 will be strained more than the other free portion, creating a tendency to tilt or disposition the unevenly contacted ramp surface 23 leading to an eccentric pump connection. Such an eccentric connection often is the causal factor that generates step or gap at the interface that leads to thrombus formation. This drawback is remedied by having the collar contour 41 of the distal flange of the coupler 40 configured in such a way that the locking engagement simultaneously includes all circumferential contact areas. When locked, the edge of the metallic beak 51 will sink slightly into the compressed silicone ramp 23 with controlled depth and further reduces the interface discontinuity when exposed to blood stream. Hence, the conventional interface thrombus can be substantially minimized or annihilated by administrating a moderate anticoagulant regimen.

Figure 10:
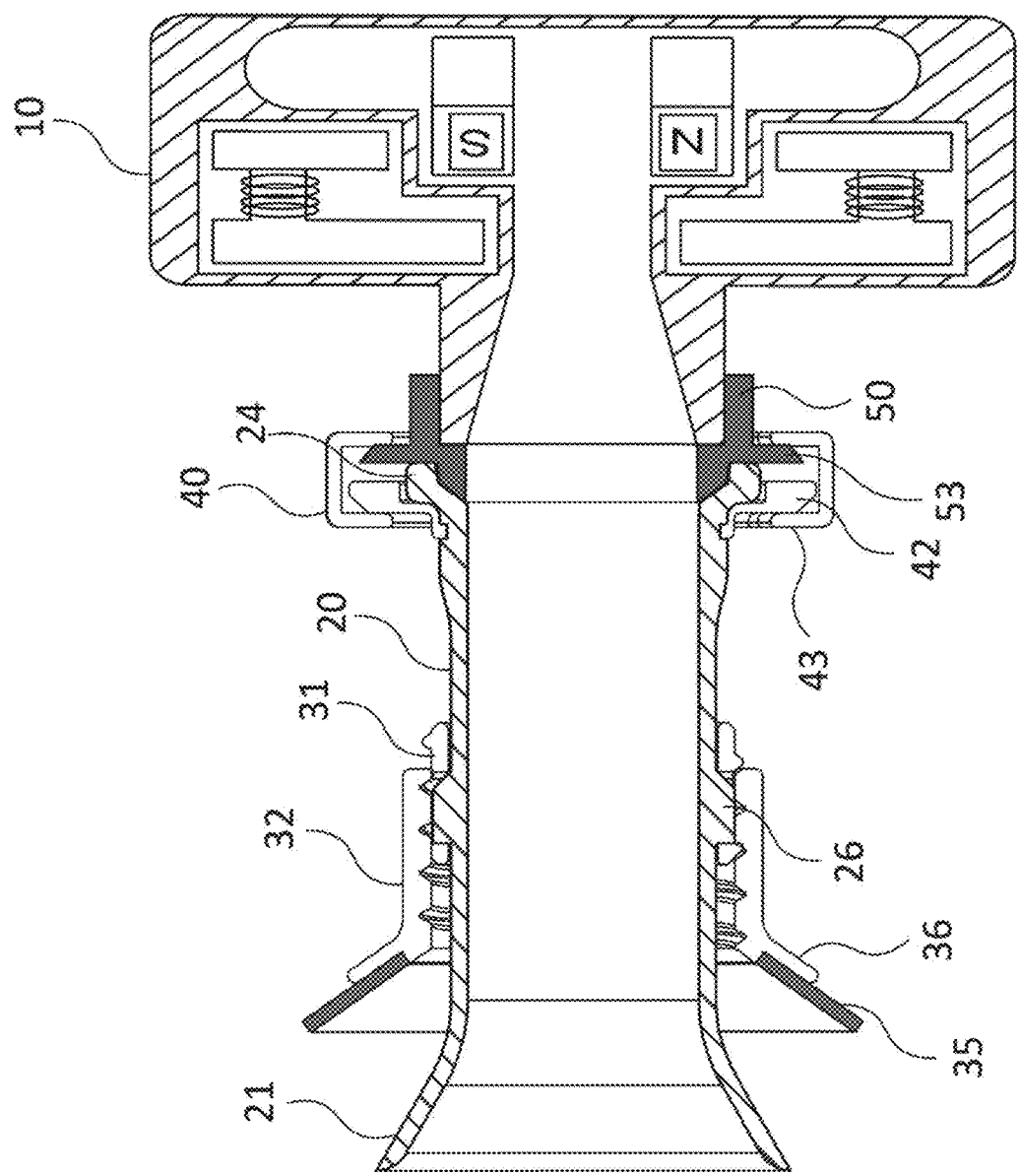
FIG. 10 is a sectional view of the coupler in a locked position connecting flow cannula, coupler flange base, and VAD inlet adapter. For clarity, velour on flow cannula conduit is not shown.

Integration of the inflow cannula 20 to the VAD 10 is accomplished by a clamping mechanism using the deformable cannula proximal end 24 serving as a "gasket" between the connected rigid flanges 42, 53 of the coupler 40 and the VAD inlet adapter 50, respectively. FIG. 10 illustrates an integrated relationship between the joined inflow cannula 20 and the inlet adapter 50 of the VAD 10, locked together by the coupler 40. The present interface connection between pump and cannula has two hemodynamic merits for reducing thrombus formation in-situ. First, there will be literally no obvious step or gap type joint discontinuities generated as observed in the conventional butt connection. Second, stasis flow located in the interface of the beak leading-edge 56 can be minimized. Hence, blood stream flowing over the connection interface will be maintained with high-speed, substantially improving the butt connection drawback, namely the forward- or backward-facing step existing at the interface, that generates flow stasis and promotes thrombotic adverse events in-situ and in the blood stream.

Implantation of the present inflow cannula invention 20 and connection of said cannula 20 to rotary blood pump 10 are summarized below. The step-by-step procedural instructions that enable such implantation are described as follows:

1. Fold the cannula 20 into a smaller profile using a crimper or by hand and tighten the folded cannula 20 around the proximal and distal ends respectively using string constraint or by snaring;
2. Core a through-hole 61 in the myocardial wall (of ventricle or atrium);
3. Insert crimped cannula across cored through-hole 61 into ventricle (or atrium). Trocar can be used to assist cannula insertion. Remove trocar after insertion;
4. Mount male and female fasteners 31, 32 sequentially onto the crimped cannula body 22 from the proximal cannula end 24;
5. Release distal string constraint to let bellmouth 21 self-expand and resume its original form;
6. Release proximal string constraint to let cannula 20 resume its original form;
7. Anchor male fastener 31 onto the protruded seats 26 on the cannula body 22;
8. Screw tighten female fastener 32 until the designated compression force on epicardium is attained. Torque wrench can be used to control the compression force;
9. Mount coupler 40 onto cannula 20 from the proximal end 24 of the cannula;

10. Prime blood pump with heparin saline for air removal;
11. Prime heart chamber and cannula interior with heparin saline to dispel the air contained;
12. Connect blood pump inlet adapter 50 with cannula proximal end 24 by closing the collars 43 of the coupler 40. Inject saline while connecting together the pump and cannula to ensure air is not entrained.

In summary, an embodiment of the present disclosure provides an inflow cannula assembly, for transporting blood between a heart chamber and a ventricular assist device (VAD), which includes a deformable polymeric cannula, a pair of male and female fasteners, a VAD coupler, a VAD inlet adapter, and a VAD inlet adapter. The cannula includes: a first end, with a bellmouth intake to be inserted into heart chamber; a second end, with a flange ramp; and a conduit, wherein the first and second ends are integrally joined by the conduit, and the entire inner surface of the cannula is smooth and seamless. The male and female fasteners are screw interconnected with the male fastener anchored on the cannula. The second end is configured to interface with the VAD inlet adapter. The VAD coupler connects the second end with the VAD inlet adapter, and the VAD coupler includes a flange base and a pair of collars pinned on the flange base, wherein the collars have an internal grooved slots to receive and compress the sandwiched flange base, the flange ramp of the cannula, and a beak flange of the VAD inlet adapter; and the VAD inlet adapter includes a wedge-shaped beak to be interfaced with the cannula's second end, the beak flange to be accepted by the coupler, and a base integrated with the VAD.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

It will be apparent to those skilled in the art that various modifications and variations can be made in the invention. It is intended that the standard and examples be considered as exemplary only, with the true scope of the disclosed embodiments being indicated by the following claims and their equivalents.

What is claimed is:

1. An inflow cannula assembly, for transporting blood between a heart chamber and a ventricular assist device (VAD), comprising:
    a deformable polymeric cannula, wherein the cannula includes:
    a first end, with a bellmouth intake to be inserted into heart chamber;
    a second end, with a flange ramp; and
    a conduit, wherein the first and second ends are integrally joined by the conduit, and the entire inner surface of the cannula is smooth and seamless;
    a pair of male and female fasteners, wherein the male and female fasteners are screw interconnected with the male fastener anchored on the cannula;
    a ventricular assist device (VAD) coupler having a sandwiched flange base and a pair of collars pinned on the sandwiched flange base; and
    a ventricular assist device (VAD) inlet adapter having a beak flange,
    wherein the second end is configured to interface with the VAD inlet adapter, and the VAD coupler connects the second end with the VAD inlet adapter;
    wherein the beak flange is accepted by the VAD coupler, and the collars have at least one internal grooved slot to receive and compress the sandwiched flange base, the flange ramp of the cannula, and the beak flange of the VAD inlet adapter; and
    wherein the VAD inlet adapter further includes a wedge-shaped beak to be interfaced with the second end and a base configured to be integrated with the VAD.

2. The inflow cannula assembly as claimed in claim 1, wherein the bellmouth has a gradually thinning wall thickness toward its tip, and the tip is sharp-edged.

3. The inflow cannula assembly as claimed in claim 1, wherein an overlay portion of the conduit is configured to be in contact with cored myocardium is roughened so as to promote cell and tissue ingrowth for hemostasis and immobilization purposes.

4. The inflow cannula assembly as claimed in claim 1, further comprising a female fastener cap configured to be in contact with an epicardium, wherein the female fastener cap is coated with a porous material.

5. The inflow cannula assembly as claimed in claim 4, further comprising a Nitinol stent, such that the female fastener cap is supported by the Nitinol stent so as to generate a spring load when locked on the epicardium, allowing the female fastener cap be always attached on the epicardium.

6. The inflow cannula assembly as claimed in claim 1, wherein the beak of the VAD inlet adapter and the second end are interfaced over the flange ramp, with the inner diameter of the beak slightly larger than the inner diameter of the conduit, wherein an interface surface of the flange ramp is inclined generally 30 to 60 degrees to a centerline of the cannula.

7. The inflow cannula assembly as claimed in claim 1, wherein the VAD coupler includes an anti-decoupling latch and a collar contour that catches simultaneously onto the entire peripheral rim of the sandwiched flange base to assure a concentric coupling between the second end and the inlet adapter of the connected VAD.

8. The inflow cannula assembly as claimed in claim 1, further comprising a stent embedment disposed in the cannula wall.

9. The inflow cannula assembly as claimed in claim 8, wherein the stent is made of Nitinol material.

10. The inflow cannula assembly as claimed in claim 8, wherein the stent has a zig-zag ring structure, and the stent is distributed over regions covering the bellmouth and the conduit.

11. The inflow cannula assembly as claimed in claim 8, wherein the stent includes a plurality of arrays of zig-zag rings, wherein the arrays of zig-zag rings having a tubular shape being disposed in the conduit and a cone-shaped array of zig-zag rings disposed in the bellmouth.

* * * * *